United States Patent
Wulff et al.

(10) Patent No.: US 6,201,164 B1
(45) Date of Patent: Mar. 13, 2001

(54) HYDROCOLLOID WOUND GEL

(75) Inventors: Trine Wulff; Sven Per Magnus Aagren, both of Humlebaek; Peter Sylvest Nielsen, Vaerloese, all of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/147,506

(22) PCT Filed: Jul. 2, 1997

(86) PCT No.: PCT/DK97/00292

§ 371 Date: Jan. 11, 1999

§ 102(e) Date: Jan. 11, 1999

(87) PCT Pub. No.: WO98/02196

PCT Pub. Date: Jan. 22, 1998

(30) Foreign Application Priority Data

Jul. 11, 1996 (DK) .................................................. 0779/96

(51) Int. Cl.[7] ...................................................... A61F 13/00
(52) U.S. Cl. ................................ 602/48; 602/41; 602/43
(58) Field of Search .................................. 602/48, 41, 43

(56) References Cited

FOREIGN PATENT DOCUMENTS

| 0 512 855 | 11/1992 | (EP) . |
| 0 567 311 | 10/1993 | (EP) . |
| 0 576 523 | 1/1994 | (EP) . |
| WO94/15562 | 7/1994 | (WO) . |
| WO95/17166 | 6/1995 | (WO) . |

OTHER PUBLICATIONS

Journal of Pharmaceutical Sciences, Apr. 1990, vol. 79, No. 4 pp. 312–316.

Primary Examiner—Michael A. Brown
Assistant Examiner—Lalita Hamilton
(74) Attorney, Agent, or Firm—Jacobson, Price, Holman & Stern, PLLC

(57) ABSTRACT

A hydrocolloid gel composition, especially a wound gel composition, which comprises: a) a water insoluble, water swellable cross-linked cellulose derivative; b) an alginate; and c) distilled water in a sufficient amount to make up the difference between the amount of ingredients a)+b) and 100% and wherein the gel comprises from 0.05 to 5.00% by weight of alginate, shows better absorption capacity than known gels, accelerates the healing by serving as a slow-release system for active ingredients promoting wound healing.

12 Claims, 8 Drawing Sheets

HYDROCOLLOID WOUND GEL

FIELD OF THE INVENTION

The present invention relates to a hydrocolloid wound gel. It also relates to a wound dressing containing a hydrocolloid wound gel and a method for preparing a hydrocolloid wound gel useful for cleansing and debriding wounds, a dressing containing a hydrocolloid wound gel useful for cleansing and debriding wounds as well as a method for treating a wound comprising applying a hydrocolloid wound gel to a wound, in particular for filling of cavities of wounds or applying a dressing containing a hydrocolloid gel over the wound as well as the use of the hydrocolloid gel as vehicle for transplantation of cells.

BACKGROUND OF THE INVENTION

It is well known that when treating chronic and acute wounds like venous stasis ulcers, pressure sores, open surgical wounds and burns it is a primary goal to reduce the healing time. Speeding-up of the healing may be obtained by cleansing and debriding of the wound combined with an effective removal of wound exudate. Commonly used wound dressings comprise gauze, foams, sponges, cotton pads or other fibrous materials. Gauze and other fibrous materials may absorb fluids by capillary action but implies, however, the disadvantages that fibres of the gauze or other fibrous materials may adhere to the new tissue causing damage to the newly formed tissue when removing the gauze or fibrous material causing wound injury on removal.

Amorphous hydrogels is a category of products used for debridement. These gels function by keeping the wound moist and thereby enhancing autolytic debridement of necrotic tissue by enzymes generated in the body by e.g. inflammatory cells.

A too aggressive debridement can impair the healing as some of the active components may be cytotoxic. Furthermore, other ingredients of a gel, e.g. preserving agents or active agents or other constituents may also be cytotoxic and may hamper the healing.

Often polyols are used for amorphous hydrogels as bacteriostatic agents, but are known for being potential allergenic, see e.g. Journal of Pharmaceutical Sciences 1990;79:312–316, Arch Dermatol. 1979;115:1451, CUTIS, 1978;21:166–178, and Contact Dermatitis 1980;6:341–144.

EP 0 567 311 A2 discloses a hydrocolloid wound gel composition which is stated to cleanse and debride wounds and to have some exudate absorbing capacity, said gel containing from about 0.005% to 1.0% by weight of a pectin, from about 2.0% to 4.5% sodium carboxymethylcellulose, from about 15.0% to 20.0% by weight of propylene glycol and the remainder substantially water to make 100% by weight.

EP 0 576 523 B1 discloses a wound dressing comprising a gel containing a water-insoluble, water swellable cross-linked cellulose derivative, water and a polyol component wherein the cellulose derivative comprises less than 10% by weight of the gel. The dressing may contain additional debriding agents, e.g. enzymatic debriding agents and/or growth factors.

EP 0 512 855 A2 discloses an absorbant wound filler comprising a polymeric matrix containing one or more styrene radial or block copolymers, one or more polyisobutylenes and mineral oil and absorbing powders comprising sodium/calcium alginates, optionally cross-linked sodium carboxymethylcellulose, optionally absorbent polyacrylates and optionally water soluble hydrocolloids. The role of the matrix is to hold the absorbing powders and the polyisobutylene helps to bind the powders in the polymeric network and mineral oil is a plasticizer for the styrene radial or block copolymer component.

WO 95/17166 discloses a wound hydrating gel comprising a hydrocolloid system comprising carboxymethylcellulose, sodium alginate/calcium alginate and a preservation system in which is preferably used a self-gelling Na/Ca alginate having about 6–7% sodium minerals and about 2.5–3.5% calcium minerals.

BRIEF DESCRIPTION OF THE INVENTION

The present invention relates to an amorphous hydrocolloid gel composition comprising a water insoluble, water swellable cross-linked cellulose derivative and an alginate.

The invention also relates to a dressing comprising an amorphous hydrogel containing a water insoluble, water swellable cross-linked cellulose derivative and an alginate.

Furthermore, the invention relates to a method for preparing a hydrocolloid gel composition comprising a water insoluble, water swellable cross-linked cellulose derivative and an alginate.

The invention also relates to a method for preparing a dressing containing an amorphous hydrocolloid gel composition comprising a water insoluble, water swellable cross-linked cellulose derivative and an alginate useful for cleansing and debriding wounds.

Further, the invention relates to the use of an amorphous hydrocolloid wound gel composition comprising a water insoluble, water swellable cross-linked cellulose derivative and an alginate for cleansing and debriding wounds as well as a method for treating a wound comprising applying a hydrocolloid wound gel composition comprising a water insoluble, water swellable cross-linked cellulose derivative and an alginate to a wound, in particular for filling of cavities of wounds or applying a dressing containing a hydrocolloid wound gel composition comprising a water insoluble, water swellable cross-linked cellulose derivative and an alginate over the wound.

Still further, the invention relates to the use of an amorphous hydrocolloid wound gel composition comprising a water insoluble, water swellable cross-linked cellulose derivative and an alginate as vehicle cells to be transplanted onto a wound.

BRIEF DESCRIPTION OF THE DRAWINGS

The invention is explained more in detail below with reference to the drawings, in which.

DETAILED DESCRIPTION OF THE INVENTION

Figure 1:
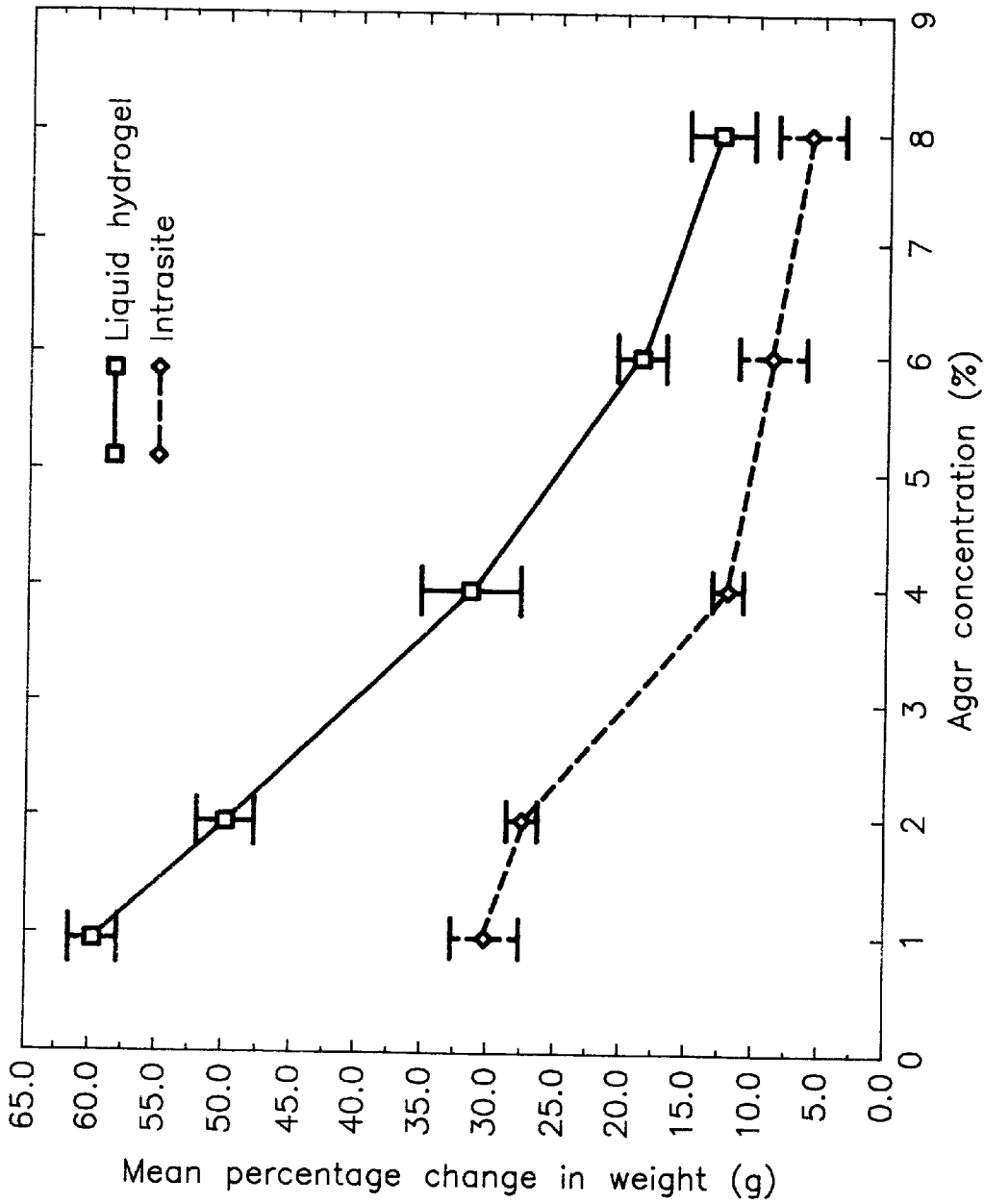
FIG. 1 is a graphical presentation of a comparison of a gel according to the invention and a commercial gel with respect to exchange of fluid in contact with agar.

The invention relates to an amorphous hydrocolloid gel composition which comprises a. a water insoluble, water swellable cross-linked cellulose derivative b. an alginate; and c. distilled water in a sufficient amount to make up the difference between the amount of ingredients a.+b. and 100% and wherein the gel comprises from 0.05 to 5.00% by weight of alginate.

The alginate may be an alkali metal or alkaline earth metal alginate such as sodium alginate or potassium alginate or calcium alginate, preferably calcium alginate being insoluble in water.

A water insoluble, water swellable cross-linked cellulose derivative is preferably cross-linked sodium carboxymethylcellulose, CMC. The cellulose derivative is preferably used in the form of a powder.

It has surprisingly been found that a hydrocolloid gel of the invention comprising an alginate and a water insoluble, water swellable cross-linked cellulose derivative shows excellent debriding and superior absorption properties and speeds up debridement of necrotic tissue in chronic wounds and speeds up the healing of the wound.

The addition of potential antigenic components is minimised in the hydrocolloid gel according to the invention.

Thus, the addition of propylene glycol being present in the formulation disclosed in EP 0 567 311 A2, or the addition of a polyol in the form of a dihydroxy alkane as disclosed in EP 0 576 523 B1 which may give concern due to the toxicity and/or antigenicity of these compounds is not necessary according to the present invention. The addition of mineral oil as disclosed in EP 0 512 855 A2 may also be avoided according to the present invention.

Furthermore, it has been found that the formulation according to the invention shows a better performance in that it gives rise to a better absorption capacity and the same ability of debriding and a more rapid healing than the known hydrocolloid wound gels.

Thus, the hydrocolloid wound gel according to the invention differs from the wound hydrating gel disclosed in WO 95/17166 in that the gel of the invention comprises a cross-linked cellulose derivative and an alginate wherein the amount of cellulose derivative is greater than the amount of alginate. It has surprisingly been found that the gel of the present invention is superior as compared with the wound hydrating gel disclosed in WO 95/17166 as it shows a much higher absorption of fluid in a moist environment.

It is preferred that the hydrocolloid gel composition of the invention comprises from 0.05 to 25.00% by weight of water insoluble, water swellable cross-linked cellulose derivative, more preferred from 0.1 to 15% by weight of water insoluble, water swellable cross-linked cellulose derivative and preferably from 1 to 5% by weight of water insoluble, water swellable cross-linked cellulose derivative.

The hydrocolloid gel composition of the invention preferably comprises from 0.05 to 5.00% by weight of alginate.

The viscosity of a hydrogel of the invention for debridement of wounds will advantageously be in the range from about 450,000 cPs to about 2,500,000 cPs and will preferably be in the range of 500,000 to about 2,000,000 cPs when determined using a Brookfield Helipath Spindle T-F, 2.5 rpm at ambient temperature.

The viscosity of a hydrogel of the invention for cell transplantation purposes will advantageously be in the range from about 1,500 to about 300,000, preferably from about 2,000 to about 200,000 cPs when determined using a Brookfield Helipath Spindle T-F, 2.5 rpm at ambient temperature.

The hydrocolloid gel of the invention may comprise wound healing associated indicator(s), cushions or similar device for treatment or prophylaxis of formation of wounds and/or skin abnormalities. This opens for a concomitant medical treatment of the wound are an easy and non-contaminating application of the active ingredients, e.g. by incorporating active ingredients such as a cytochine such as growth hormone or a polypeptide growth factor giving rise to the incorporation of such active substances in a form being apt to local application in a wound in which the medicament may exercise its effect on the wound, other medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate or silver chloride, zinc or salts thereof, metronidazol, sulpha drugs, and penicillins, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as II-lostat or ethylene diamine tetraacetic acid, cytotoxic agents and proliferation inhibitors for use in for example surgical insertion of the product in cancer tissue and/or other therapeutic agents which optionally may be used for topical application, pain relieving agents such as lidocaine or chinchocaine, emollients, retinoids or agents having a cooling effect which is also considered an aspect of the invention.

In accordance with another aspect of the invention hydrocolloid gel composition comprises an enzyme enhancing the debridement of wounds. Preferably, the enzyme is Krill enzyme.

In the present context growth hormone is intended to designate any growth hormone which is applicable in accordance with the invention such as human, bovine ovine, porcine, equine, salmon or tuna growth hormone or analogues or derivatives thereof such as shortened or extended growth hormones such as methionyl growth hormone. A growth hormone is preferably human growth hormone.

Wound healing associated indicator(s) may e.g. be indicators of pH, partial pressure of $O_2$, temperature, radical mechanisms or biotechnological assays, e.g. indicating formation and/or degradation of collagen.

The hydrogel may be applied directly into the wound to be treated and is then suitably covered by a cover dressing having a suitable moisture vapour transmission rate to avoid a drying of the wound in order to ensure a moist wound healing. One suitable cover dressing for a hydrogel according to the invention is sold under the trademark Tegaderm®. Other suitable cover dressings are e.g. Comfeel® Plus Ulcer Dressing or Comfeel® Plus Transparent Dressing.

The hydrogel of the invention may be applied in a gauze pad or a pad of a non-woven or woven material or in an open cell foam dressing.

In another aspect the invention relates to a method for preparing a hydrocolloid gel formulation wherein a cross-linked, water insoluble, water swellable cross-linked cellulose derivative, preferably carboxymethylcellulose derivative, is mixed with water and an alginate powder.

The mixing may be carried out using a dissolver or another suitable mixer which enables the admixture of the water and formation of the hydrogel. In a further aspect the invention relates to a wound dressing comprising a hydrocolloid gel containing a water insoluble, water swellable cross-linked cellulose derivative, an alginate; and distilled water in a sufficient amount to make up the difference between the amount of the other ingredients and 100% and wherein the gel comprises from 0.05 to 5.00% by weight of alginate.

Further, the invention relates to a wound dressing comprising a gel containing a water insoluble, water swellable cross-linked cellulose derivative, an alginate; and distilled water in a sufficient amount to make up the difference between the amount of the other ingredients and 100% and wherein the gel comprises from 0.05 to 5.00% by weight of alginate.

The hydrogel of the wound dressing of the invention preferably comprises from 2.00 to 8.00% by weight of cross-linked sodium carboxymethylcellulose, more preferred from 3 to 5% by weight of water insoluble, water swellable cross-linked cellulose derivative.

The contents of an alginate in the hydrogel in a dressing of the invention is preferably from 0.5 to 1.00%, more preferred 0.1–2%, by weight of alginate, preferably calcium alginate.

A dressing according to the invention comprising a hydrocolloid gel containing a water insoluble, water swellable cross-linked cellulose derivative, an alginate; and distilled water in a sufficient amount to make up the difference between the amount of the other ingredients and 100%, wherein the gel comprises from 0.05 to 5.00% by weight of alginate may e.g. be prepared in an analogous manner as disclosed in WO 94/15562.

In a further aspect the invention relates to a vehicle for use for transplantation of cells to a wound, said vehicle comprising an amorphous hydrocolloid gel composition which comprises
 a. a water insoluble, water swellable cross-linked cellulose derivative
 b. an alginate; and
 c. distilled water in a sufficient amount to make up the difference between the amount of ingredients a.+b. and 100% and wherein the gel comprises from 0.05 to 5.00% by weight of alginate.

In yet a further aspect, the invention relates to the use of an amorphous hydrocolloid gel composition which comprises
 a. a water insoluble, water swellable cross-linked cellulose derivative
 b. an alginate; and
 c. distilled water in a sufficient amount to make up the difference between the amount of ingredients a.+b. and 100% and wherein the gel comprises from 0.05 to 5.00% by weight of alginate for debridement of necrotic tissue in a wound and for speeding up the healing of the wound.

Still further, the invention relates to the use of an amorphous hydrocolloid gel composition which comprises
 a. a water insoluble, water swellable cross-linked cellulose derivative
 b. an alginate; and
 c. distilled water in a sufficient amount to make up the difference between the amount of ingredients a.+b. and 100% and wherein the gel comprises from 0.05 to 5.00% by weight of alginate as vehicle for transplantation of cells to a wound.

The invention is illustrated more in detail in the below examples which are provided to illustrate presently contemplated preferred embodiments and the best mode for practising the invention, but are not intended to be limiting thereof.

Experimental Part

Materials and Methods

SMTL test method TM-70 (Surgical Materials Testing Lab., "Fluid Exchange in Hydrogel Dressings").

Used to determine the ability of a hydrogel to absorb liquid from or donate liquid to a semisolid substance.

Determination of epithelialization was carried out as described by Agren M. (Br J Plast Surg 1996;49:129–134)

Determination of viscosity was carried out using a Brookfield, Helipath Spindle T-F, 2.5 rpm, ambient temperature.

Carboxymethylcellulose (CMC): Cross-linked CMC (AQUASORB® A500) from Aqualon, a Division of Hercules Incorporated.

Calcium Alginate: Grindsted Alginate PH 470-S2 from Danisco Ingredients.

Agar from Oxoid.

Gelatin from Sigma $CaCl_2$ from Struers,

NaCl from Struers

Mixer Dissolver APV 60S from Grieser.

Syringes 60 ml OMNIFIX® from BRAUN

Serum-free medium: KGM from Clonetics

Ultrapure sterile water: Maxima from Elga

PBS (Phosphate buffered saline) 120 mmol/l NaCl, 2.7 mmol/l KCl, 10 mmol/l phosphate from Sigma Human skin fibroblasts: primary cultures of normal human dermis.

3% $H_2O_2$ gel: BRINT OVER ILTE GEL from Danapharm.

EXAMPLE 1

Preparation of an amorphous hydrogel according to the invention.

Hydrogels were prepared as follows: The cross-linked Carboxymethylcellulose and the calcium alginate powders were mixed in a dissolver mixer at setting 0/500 rpm corresponding to low speed using two dissolver disks. Two thirds of the calculated amount of distilled water was added, and the speed was increased to 30/2000 rpm and mixing was performed for 7 minutes. The remainder of the water was added over a period of about 5 minutes, and the speed was further increased to 60/3000 rpm and the pressure was reduced to vacuum (water pump) for 10 minutes. The resulting gel was filled into disposable syringes which were stoppered and packed in peel-bags which were welded and sterilised in an autoclave at 120 degrees C. for 20 minutes plus equalisation.

Gels having the compositions were produced shown in the below Table 1:

TABLE 1

Composition of gels according to the invention

| Gel/ Constituent | A % | grams | B % | grams |
|---|---|---|---|---|
| Cross-linked CMC | 3.31 | 993 | 4.80 | 1440 |
| Calcium alginate | 0.37 | 111 | 0.53 | 159 |
| Distilled water | 96.32 | 28896 | 94.67 | 28401 |
| Total | 100 | 30000 | 100 | 30000 |

The viscosity of the gels according to the invention as well as the viscosity of IntraSite® Gel was determined using a Brookfield viscometer and the results appear from the below Table 2.

TABLE 2

Viscosity of gels according to the invention and of IntraSite® Gel

| Gel | Viscosity in cPs |
|---|---|
| Hydrogel A | 800000 |
| Hydrogel B | 1600000 |
| IntraSite® Gel | 400000 |

EXAMPLE 2

Absorbing capacity of a hydrogel according to the invention as compared to the absorbing capacity of a commercial hydrogel.

Method

An amorphous hydrogel according to the invention was compared with a commercial hydrogel sold as IntraSite® Gel by Smith & Nephew with respect to its ability to absorb liquid from or donate liquid to a semisolid substance.

5.0±0.2 grams samples of the test material were placed inside a series of plastic chambers each resting upon a piece of nylon net having a pore size of 100 microns. The chambers were weighed and placed on the surface of a series of agar and gelatine gels of varying strength made up with a solution containing 142 mmol sodium ions and 2.5 mmol of calcium ions per liter. After 48 hours the test chambers were removed from the gels, reweighed and the absolute and the percentage change of each sample calculated.

Figure 2:
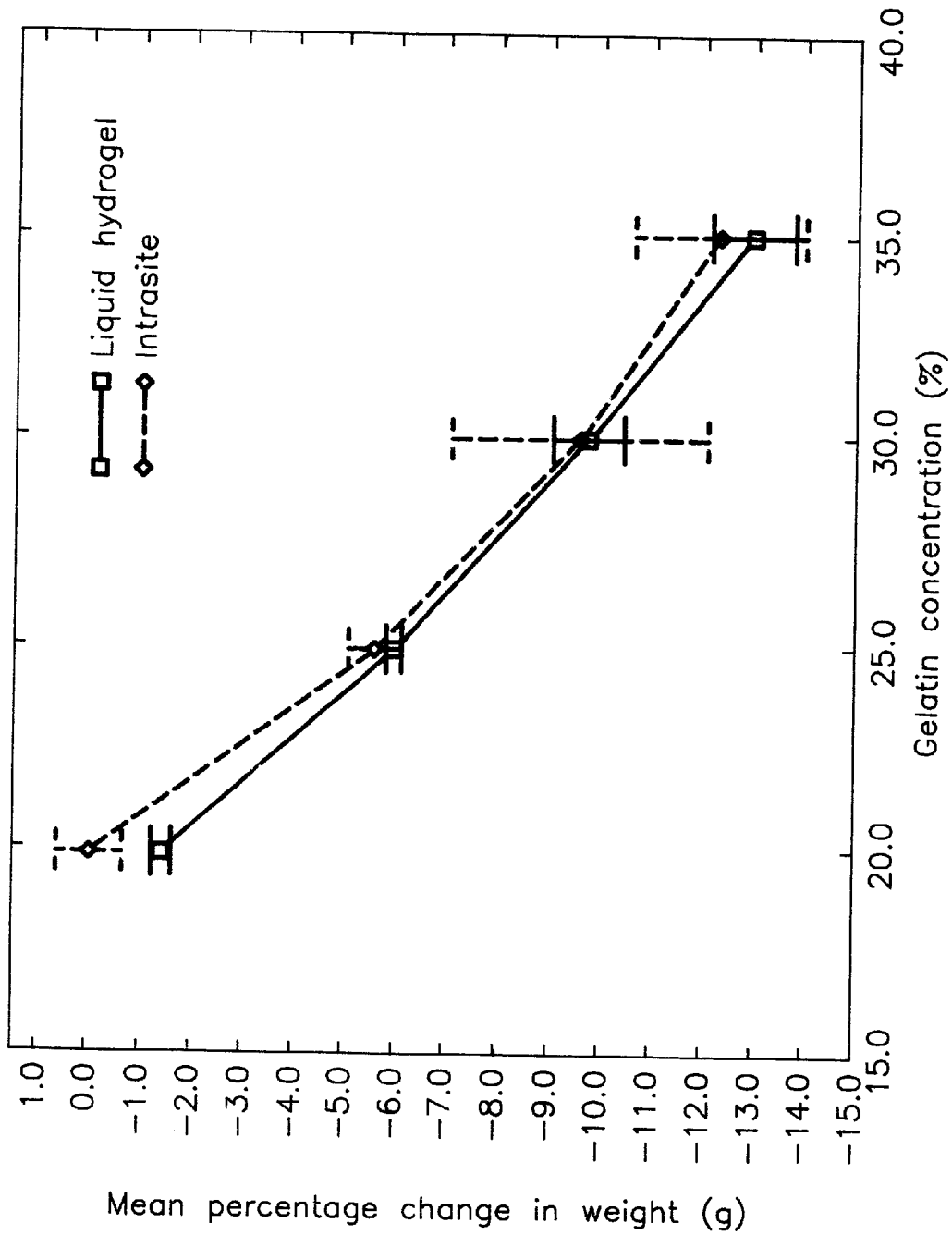
FIG. 2 is a graphical presentation of a comparison of a gel according to the invention and a commercial gel with respect to exchange of fluid in contact with gelatine.

The results of the test to determine the fluid affinity of the two hydrogels are summarised in Tables 3 and 4 below and expressed graphically in FIGS. 1 and 2.

Results

The results clearly show that the hydrogel according to the invention is superior as compared to the commercial IntraSite® Gel with respect to absorption of fluid in a moist environment (Table 3) and similar donation of fluid in a dry environment (Table 4). This is critical in the moist part of the debridement of a wound during which the gel shall have as high absorption capacity as possible to avoid leakage and maceration of the periulcer skin and still retain a high viscosity in order to remain in the wound cavity. Donation is critical when moisturising the dry necrotic tissue.

TABLE 3

Fluid affinity of hydrogel of invention and IntraSite® Gel against agar (Absorption).

| Dressing | Concentration of agar (% w/w) | Absolute increase in weight (g) | Percentage increase in weight (%) |
|---|---|---|---|
| Amorphous Hydrogel of the invention | 1 | 2.99(0.10) | 59.74(1.92) |
| | 2 | 2.49(0.11) | 49.89(2.13) |
| | 4 | 1.58(0.20) | 31.52(3.90) |
| | 6 | 0.94(0.09) | 18.73(1.86) |
| | 8 | 0.63(0.13) | 12.70(2.51) |
| IntraSite® Gel | 1 | 1.51(0.13) | 30.23(2.58) |
| | 2 | 1.38(0.06) | 27.54(1.17) |
| | 4 | 0.60(0.06) | 12.04(1.24) |
| | 6 | 0.43(0.13) | 8.69(2.55) |
| | 8 | 0.30(0.13) | 5.93(2.52) |

Figures in parentheses designates standard deviation (SD).

TABLE 4

Fluid affinity of hydrogel of invention and IntraSite® Gel against gelatine (Donation)

| Dressing | Concentration of gelatine (% w/w) | Absolute decrease in weight in gram | Percentage decrease in weight |
|---|---|---|---|
| Amorphous Hydrogel of invention | 20 | 0.07(0.01) | 1.41(0.21) |
| | 25 | 0.30(0.01) | 5.92(0.16) |
| | 30 | 0.49(0.04) | 9.72(0.70) |
| | 35 | 0.65(0.04) | 12.94(0.82) |
| IntraSite® Gel | 20 | 0.00(0.03) | 0.00(0.67) |
| | 25 | 0.28(0.02) | 5.53(0.50) |
| | 30 | 0.48(0.12) | 9.51(2.48) |
| | 35 | 0.61(0.08) | 12.25(1.67) |

Figures in parentheses designates standard deviation (SD).

EXAMPLE 3

In vitro cohesive strength of hydrogel according to the invention and a known gel Method The cohesive strength of a hydrogel is decisive for its suitability for use in an exuding wound. Good cohesion is necessary in order that the gel may remain on the wound site, also having absorbed wound exudate, preventing a spreading of wound exudate which would hamper the periulcer skin and thereby the healing.

The cohesive strength of the hydrogels was determined as published by poster presentation In-Vitro Cohesive Properties of Wound Gels at the fifth European Conference in Wound Management, Harrogate. Nov. 21–24, 1995 for undiluted gels and for gels diluted with two parts isotonic saline to simulate a situation wherein the gel has absorbed wound fluid. Six grams of gel was placed on a test cell comprising two opposite plates having an area of 1256 cm2. Firstly, the gels were compressed using a mass of 2.3 kg for 30 seconds, excess gel was removed from the sides of the test cell, and the peak force needed to separate cohesively a sample of gel was measured.

The cohesive strength of a gel according to the invention prepared as described in Example 1a was compared to the cohesive strength of a commercial gel, Intra-Site® Gel, and the results are presented in the below Table 5.

TABLE 5

Cohesion in N

| Gel Dilution | Invention Undiluted | IntraSite ® Gel Undiluted | Invention Diluted to 33% | IntraSite ® Gel Diluted to 33% |
| --- | --- | --- | --- | --- |
| Sample No. | | | | |
| 1 | 5.871 | 5.104 | 3.368 | 1.93 |
| 2 | 6.439 | 4.986 | 3.284 | 1.938 |
| 3 | 6.176 | 4.875 | 3.368 | 1.801 |
| 4 | 6.123 | 4.963 | 3.197 | 1.77 |
| 5 | 6.317 | 5.062 | 3.315 | 1.759 |
| Mean | 6.19 | 5.00 | 3.31 | 1.84 |
| SD | 0.21 | 0.09 | 0.07 | 0.09 |

SD designates Standard Deviation

It appears that the gel according to the invention has a higher cohesion than the commercial gel in an undiluted state and that the cohesion of the gel of the invention is clearly higher when diluted to 33% indication a far better ability to remain in the wound when applied to an exuding wound.

EXAMPLE 4

Inhibition of chemotaxis of a hydrogel according to the invention.

A hydrogel of the invention comprising cross-linked CMC and calcium alginate in a proportion of 4:1 and a content of CMC and alginate if in total 5.33% was prepared using the method as disclosed in Example 1B.

The chemotaxis (migration) of human skin fibroblasts and keratinocytes in vitro was measured in order to evaluate the effect of hydrogel comprising cross-linked CMC+calcium alginate.

Method

Chemotaxis of human skin fibroblasts and keratinocytes was induced by porcine wound fluid in the lower well of modified Boyden chamber. Wound fluid, wound fluid with hydrogel (0.5% w/v) and hydrogel alone were incubated for two hours at 37° C. prior to the initiation of the chemotaxtic assay. Suspended cells were then added to the upper well and the chambers were incubated for four hours at 37° C., 5% $CO_2$/air. The number of cells that had migrated through the Nuclepore® membrane (8 $\mu$m pores) were fixed and stained, the stain was extracted with 0.1N HCl, and the O.D. was measured at 620 nm.

Results

Porcine wound fluid induced a significant chemotactic (p<0.05) response in both fibroblasts and keratinocytes. The chemotactic molecule for fibroblast was most likely PDGF whereas that of the keratinocytes still are unknown as EGF (50 ng/ml), IL-1α (100 ng/ml and KGF (100 ng/ml) all failed to induce chemotaxis in the keratinocytes. Hydrogel inhibited chemotaxis significantly (p<0.55) in both systems.

Conclusion

The observed inhibition of chemotaxis in vitro of fibroblasts and keratinocytes by hydrogel components may indicate that the chemotactic molecules are sequestered by the hydrogel components. In a wound, a hydrogel according to the invention thus may function as a reservoir for biologically active molecules which are released at a rate optimal for cellular migration.

Figure 3:
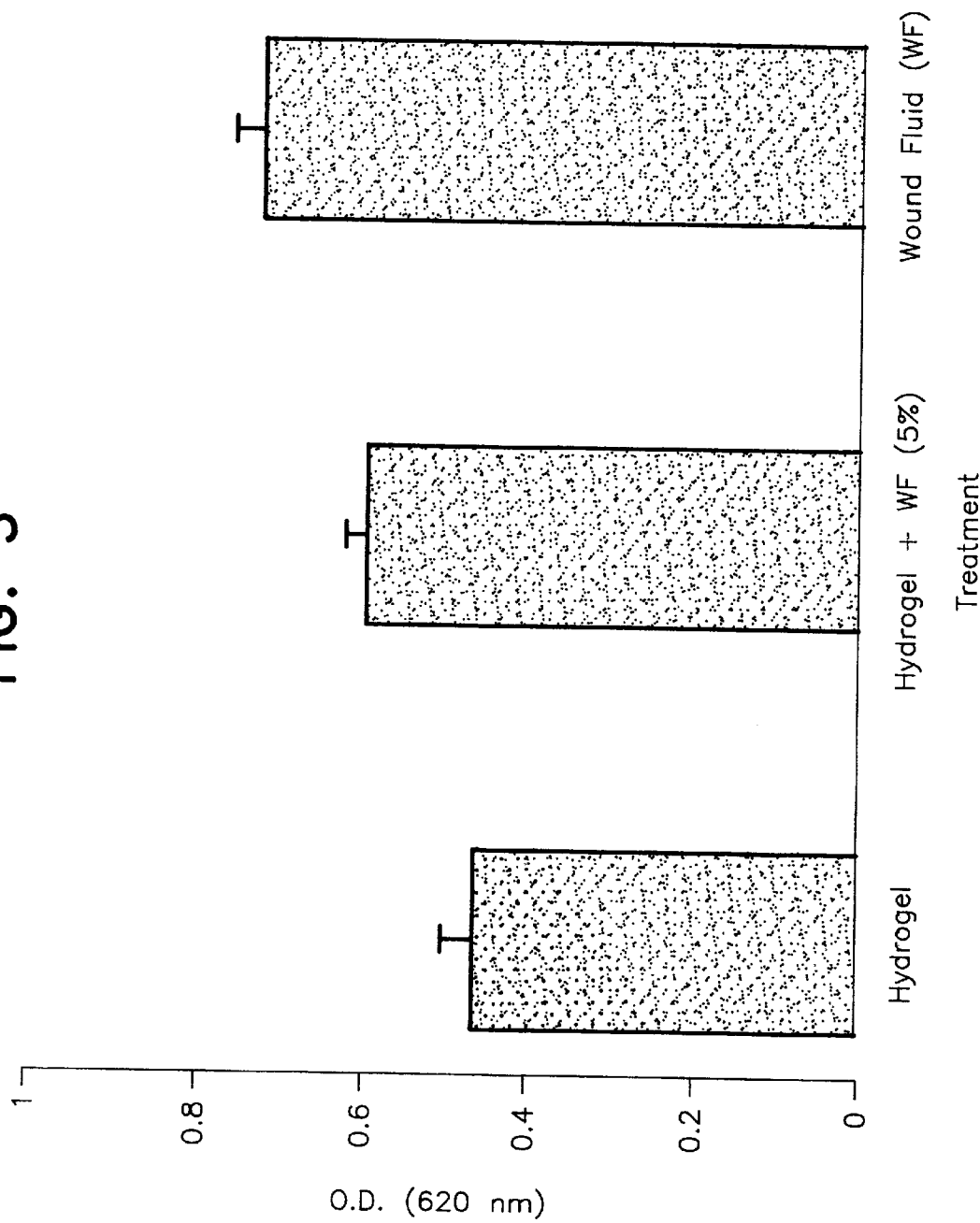
FIG. 3 is a diagram showing interference of fibroblast chemotaxis of a hydrogel according to the invention on fibroblasts in vitro.
Figure 4:
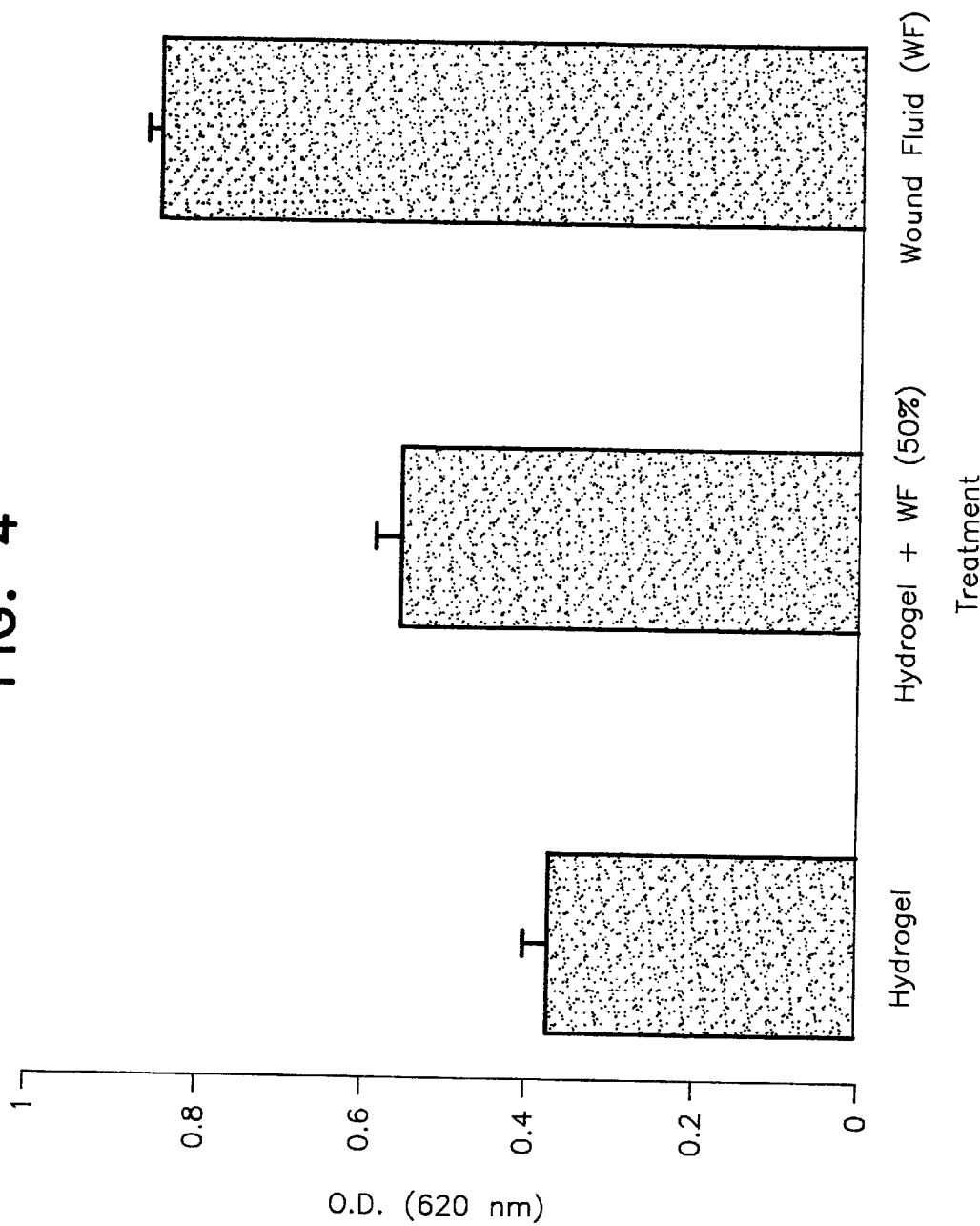
FIG. 4 is a diagram showing interference of keratinocyte chemotaxis of a hydrogel according to the invention on keratinocytes in vitro.

The results are shown in FIGS. 3 and 4 showing the determinations of O.D. for the hydrogel of the invention, hydrogel and wound fluid (WF) and wound fluid alone.

EXAMPLE 5

Effect of a hydrogel according to the invention on keratinocyte proliferation as compared to known hydrogels Method Confluent human keratinocytes grown in serum-free medium were exposed to different hydrogels (Gel according to invention, IntraSite® Gel. 3% $H_2O_2$-gel, propylene glycol) at final concentrations of 0.2%, 2% and 10% for 24 hours. Dilutions were carried out using KGM+10% ultrapure, sterile water. Control cells were treated with KGM+10% ultrapure, sterile water (final concentration). Proliferation was assessed using incorporation of the thymidine analogue bromodeoxyuridine at 10 $\mu$M (BrdU) during the 24 hour-incubation period. Incorporated BrdU was immunodetected using an ELSA-Kit from Boehringer Mannheim (Cat. No. 1 647 229).

Results

Figure 8:
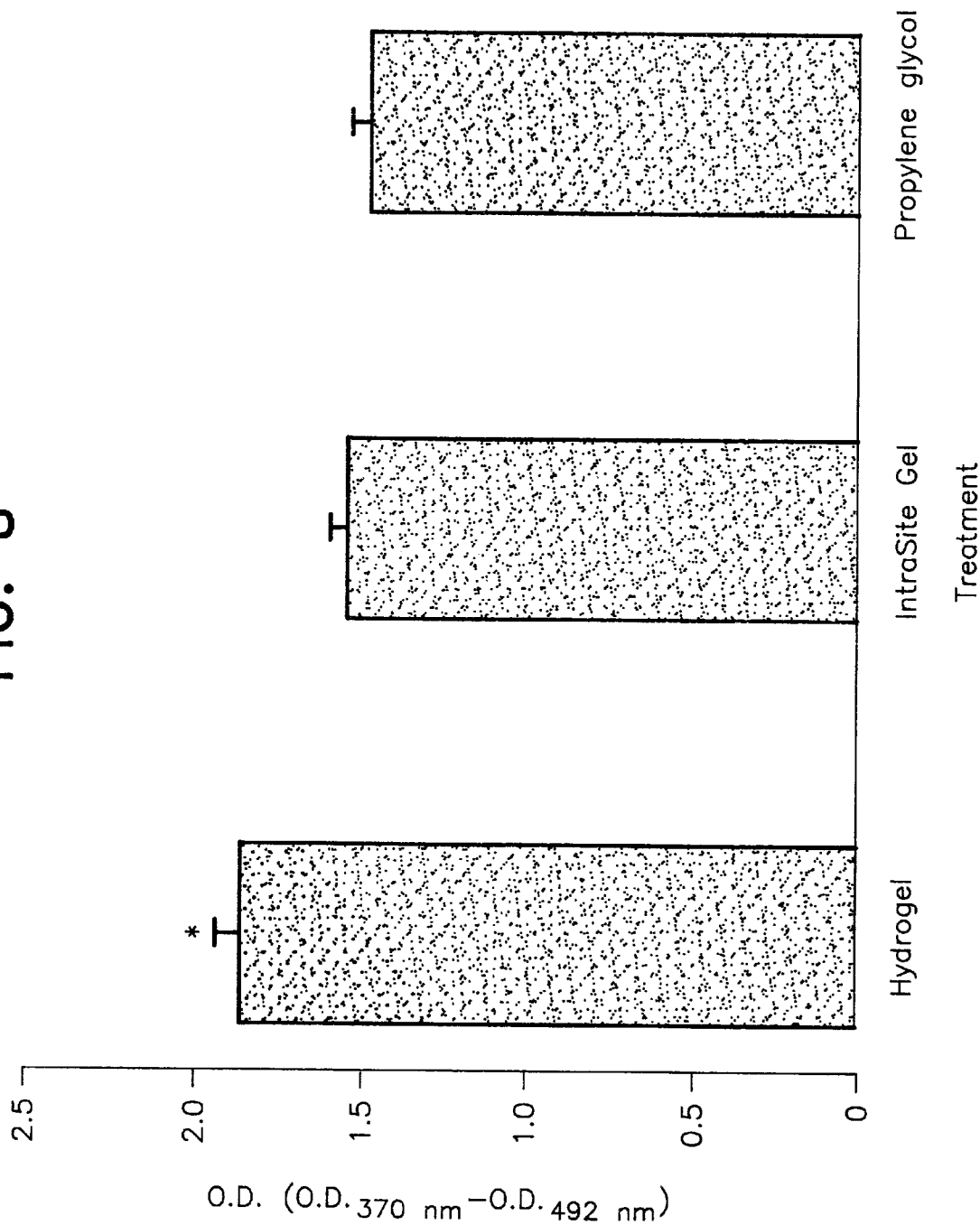
FIG. 8 is a diagram showing the effect of hydrogels on the proliferation of keratinocytes.

An inhibition of keratinocyte proliferation was found with all treatments and dosages. However, at the highest concentration (10%) the inhibition was significantly more pronounced Intrasite® Gel and propylene glycol (273 mM) than for the gel according to the invention as can be seen from FIG. 8. The $H_2O_2$-gel inhibited keratinocyte proliferation nearly 100% at all dosages.

EXAMPLE 6

The osmolality of the gels were also determined by freeze point depression and the results are presented in the below Table 6. PBS was used as control.

TABLE 6

Osmolality of gel according to invention as compared to known gels

| Gel | Osmolality |
| --- | --- |
| $H_2O_2$ gel | 2.390 osmol/kg |
| | 2.314 osmol/kg |
| Gel of invention | 0.110 osmol/kg |
| | 0.109 osmol/kg |
| IntraSite ® Gel | 3.168 osmol/kg |
| | 3.164 osmol/kg |
| | 3.248 osmol/kg ) |
| | 3.132 osmol/kg |
| PBS (Control) | 0.290 osmol/kg |
| | 0.289 osmol/kg |

The results show that the gel according to the invention is more suitable for use for wound healing and especially for transplantation of cells to wounds in order to speed up re-epithelialization as the osmolality of the gel of the invention is more similar to the isotonic and physiological osmolality which is represented by the control.

EXAMPLE 7

Effect on wound healing of a hydrogel according to the invention as compared to the effect of healing of a commercial hydrogel.

The effect on healing (re-epithelialization) in the treatment of partial thickness wounds in pigs as evaluated by a comparative study.

Method

The experiments were carried out as described in M. Agren 1996. Partial thickness wounds (2.5×2.5×0.04 cm) were made in each of six domestic pigs (60±6 kg). The treatments were allocated with two regions on each pig in a randomised manner. The first region comprised the four most cephalad wounds and the second region the most caudal wounds. The wounds were each treated with 1.5–2.0 ml of gel administered from 5 ml syringes and covered with Tegaderm® Dressing. Tegaderm® Dressing alone was used as control. On the 24th post-operative hour, the dressings were removed, the wounds were cleansed with saline, a fresh portion of gel was administered, and the wounds were again covered with Tegaderm® Dressing. The animals were killed after 66 hours and the wound sites excised and fixed using formalin. Four sections spaced 4–5 mm from each other from each wound were stained using Hematoxylin-eosin and assessed for epithelium coverage (expressed as a percentage) by light microscopy by a "blinded" investigator.

The hydrogel of the invention was produced using the method as described in Example 1 and had the following composition: 4.8% (w/v) Cross-linked CMC, 0.53% (w/v) calcium alginate and 94.67% water.

As comparison IntraSite® Gel from Smith & Nephew was used together with 3% hydrogen peroxide in poloxamer 407.

Results

Figure 5:
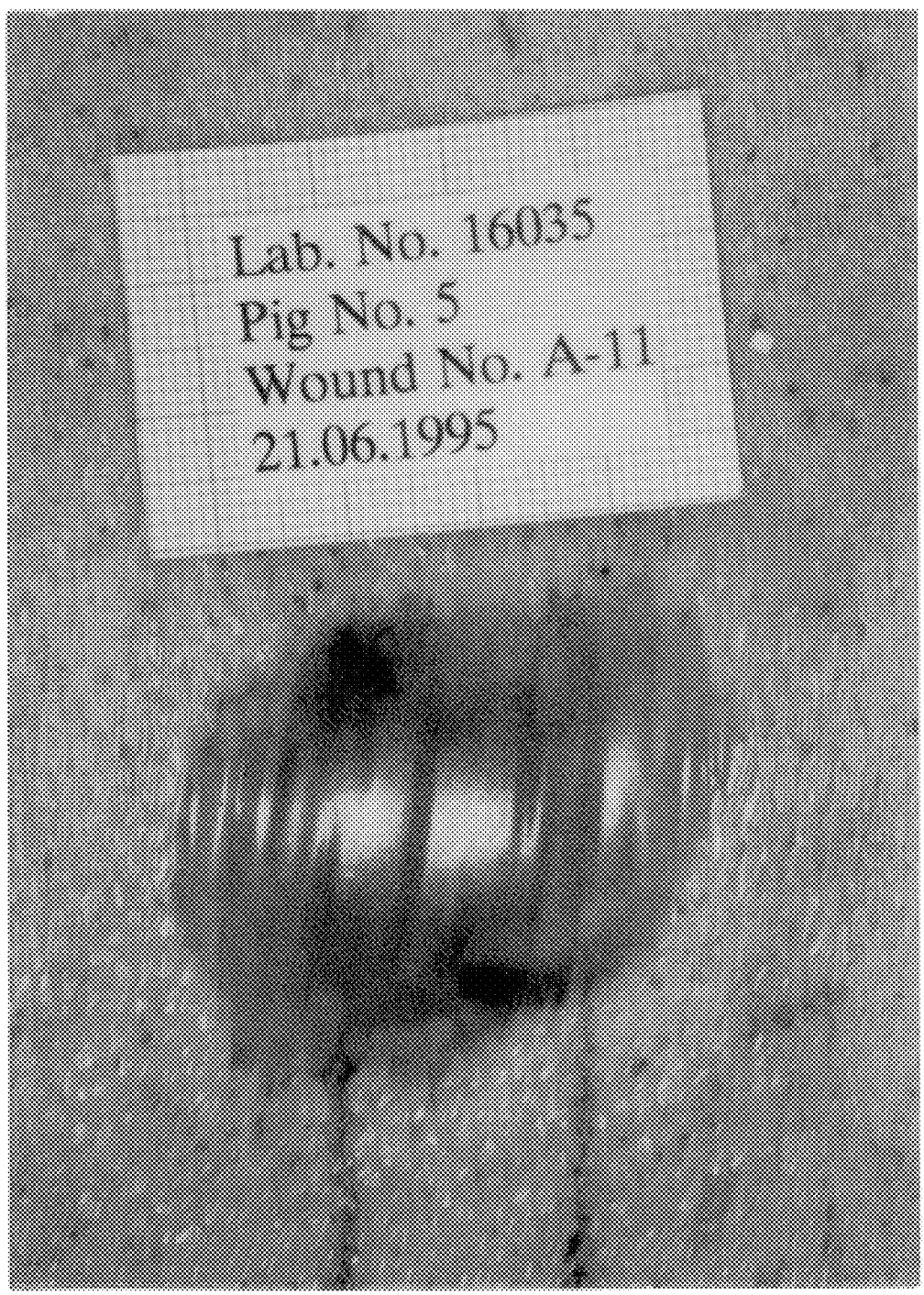
FIG. 5 is a photo showing a wound on a pig treated with the gel according to the invention after 24 hours.
Figure 6:
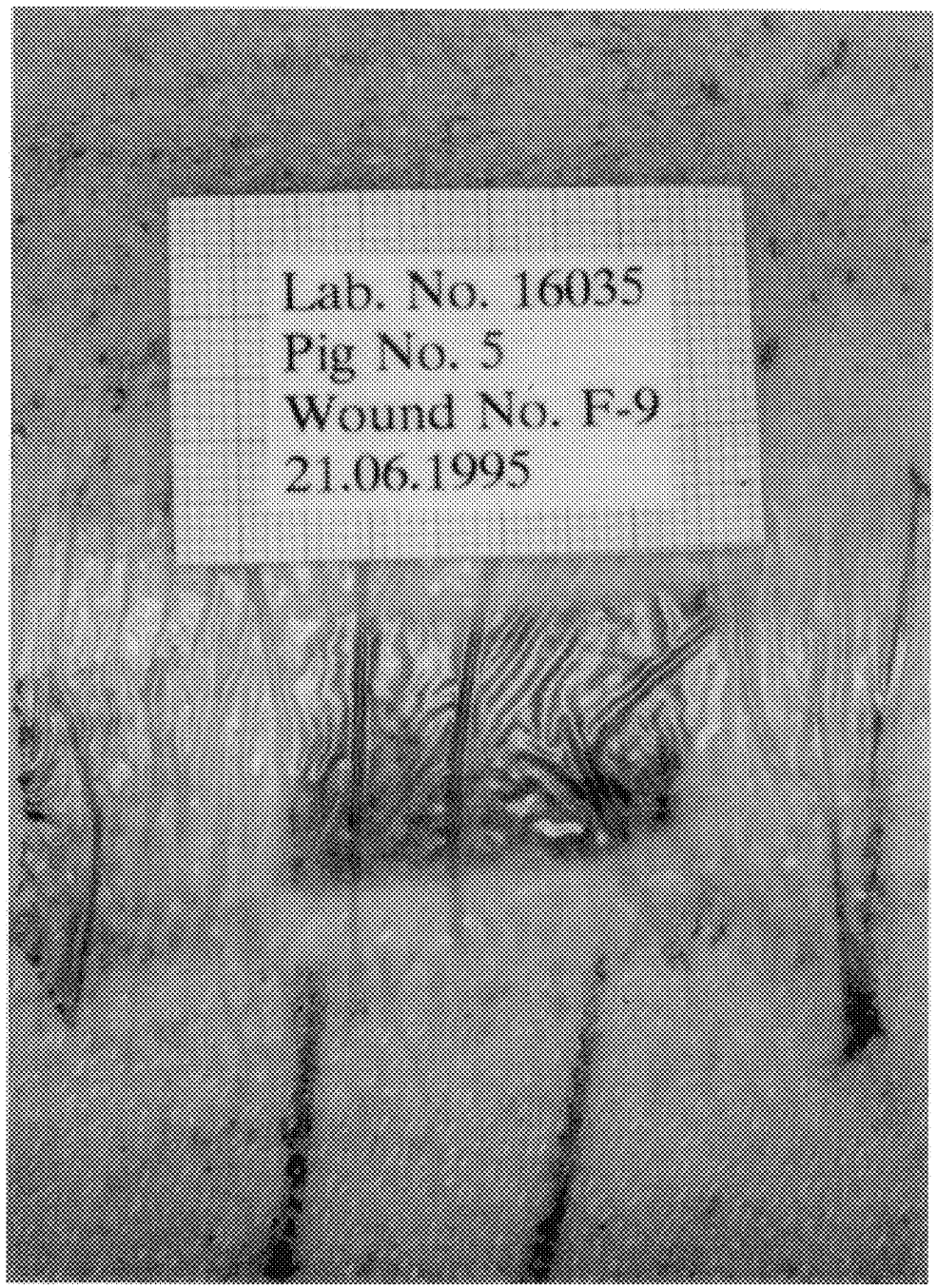
FIG. 6 is a photo showing a wound on a pig treated with a known gel after 24 hours.
Figure 7:
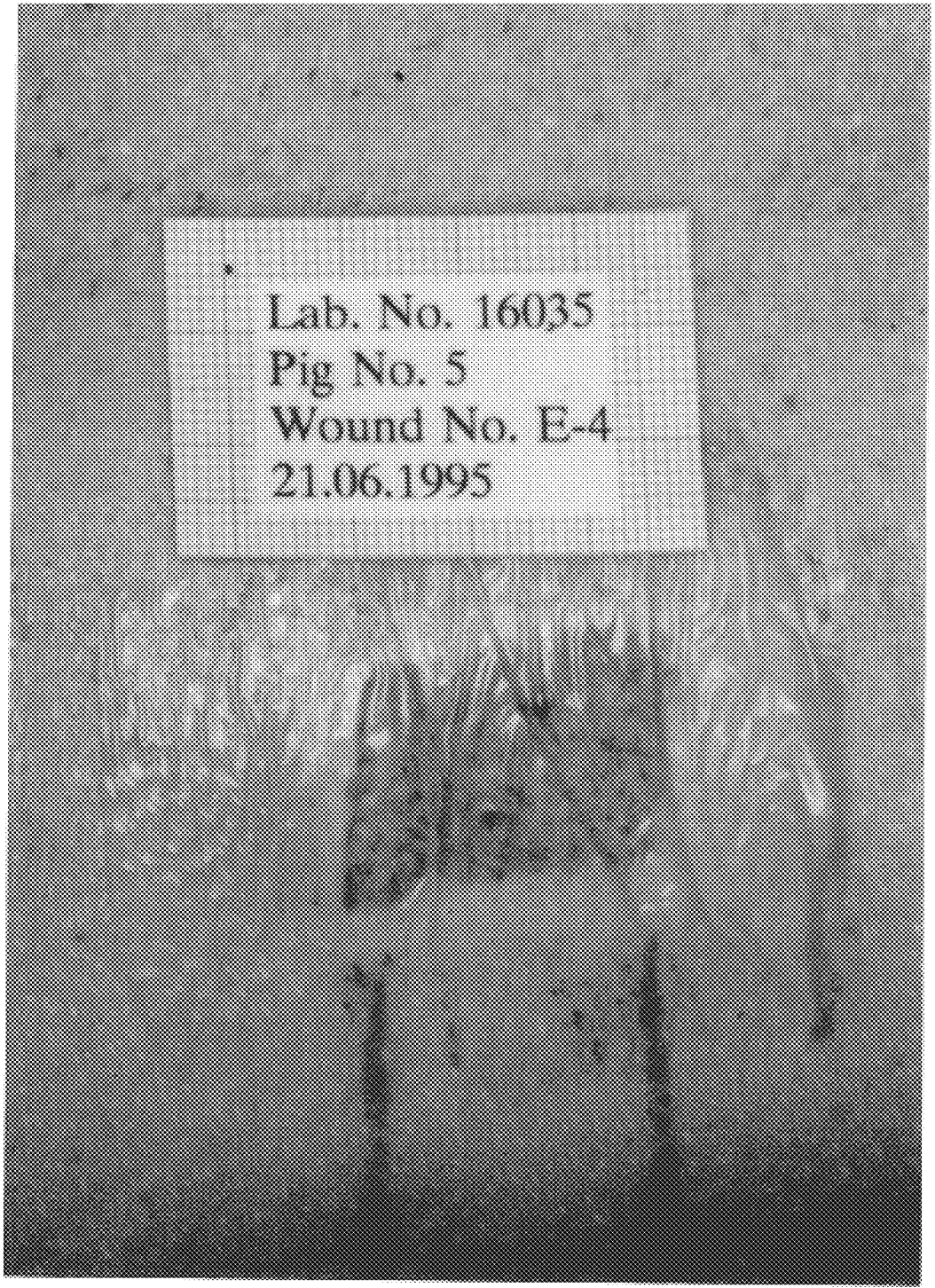
FIG. 7 is a photo showing a wound on a pig treated with the control after 24 hours.

Minor displacements (2–3 mm) of the secondary dressing was observed in one or two wounds in each animal after 24 and 66 hours. The gel according to the invention remained macroscopically intact as opposed to the other gels which had disappeared at both time points as appears from FIGS. 5–7 being photos of he wound sites after 66 hours. The results are summarised in the below Table 7. Morphometric evaluation followed by analysis of variance revealed statistically significant (p<0.05) differences between the treatments.

TABLE 7

Re-epithelialization of partial thickness wounds in pigs

| Test material | Mean Epithelial coverage (%) | 95% confidence interval |
| --- | --- | --- |
| Gel of invention | 76.6 | 66.7–84.4 |
| Control (Tegaderm ® Dressing) | 62.2 | 54.4–70.1 |
| IntraSite ® Gel | 54.5 | 46.6–62.3 |
| $H_2O_2$ gel | 53.4 | 45.5–61.2 |

Conclusions

The gel of the invention resulted in significantly higher epithelial coverage than the other treatments and the gel according to the invention accelerates epithelialization of clean superficial wounds by more than 20% as compared to the control.

EXAMPLE 8

Hydrogel according to the invention as vehicle for cells

Method

Hydrogel diluted 4 times with phosphate buffered saline (PBS) was used for these experiments (1 part gel: 3 parts PBS). Cells (human skin fibroblasts) were suspended in 0.4 ml diluted hydrogel or 0.4 ml of PBS alone to a concentration of $5 \times 10^5$ cells/ml and added to incubation wells (surface area: 2 $cm^2$) coated with monomeric type I bovine collagen, fibrillar type I bovine collagen or plastic alone (polystyrene). The cells were incubated for 4 hours at 37° C. in 5% $CO_2$ and then 1.6 ml culture medium (DMEM+10% fetal calf serum)/well was added. The 24-well plate was incubated for a further 72 hours. The medium was removed, and the cells washed with PBS, fixed and stained with Diff-Quik. The wells were photographed and slides evaluated.

Results

Fibroblasts suspended in a gel according to the invention (diluted) migrated to an artificial wound surface (collagen) to the same extent as from PBS as shown from the below Table 8.

TABLE 8

Adherent fibroblasts in PBS or in gel according to the invention after 3 days of incubation

| | Treatment | |
| --- | --- | --- |
| Surface | PBS | Gel of invention |
| Polystyrene | + | +++++ |
| Monomeric collagen | ++* | +++ |
| Fibrillar collagen | +++ | +++ |

+ = few fibroblast; +++ = many fibroblasts; +++++ = abundant of fibroblasts.
* = abnormal morphology of fibroblast.

Conclusions

This in vitro study clearly indicates that a gel according to the invention is an appropriate vehicle for fibroblasts to be transplanted to a wound. Furthermore, the gel of the invention also appears to have a beneficial and stabilising effect on cells under stress.

EXAMPLE 9

Absorbing capacity of a hydrogel according to the invention as compared to the absorbing capacity of a known hydrogel.

Method

An amorphous hydrogel according to the invention was compared with a gel known from WO 95/17166 with respect to its ability to absorb liquid from or donate liquid to a semisolid substance by the method disclosed in Example 2 using 2% Agar and 35% gelatine.

The results of the test to determine the fluid affinity of the two hydrogels are summarised in Tables 9 and 10 below.

Results

The results clearly show that the hydrogel according to the invention is superior as compared to gel known from WO 95/17166 with respect to absorption of fluid in a moist environment (Table 9) and similar with respect to donation of fluid in a dry environment (Table 10). This is critical in the moist part of wound to be debrided in which the gel shall have as high absorption capacity as possible to avoid leakage and maceration of the periulcer skin.

TABLE 9

Fluid affinity of hydrogel of invention and gel known from WO 95/17166 against agar (Absorption).

| Dressing | Concentration of agar (% w/w) | Absolute increase in weight (g) | Percentage increase in weight (%) |
| --- | --- | --- | --- |
| Amorphous Hydrogel of the invention | 2 | 2.40 | 24.00(0.26) |
| gel known from WO 95/17166 | 2 | 0.75 | 7.52(0.06) |

Figures in parentheses designates standard deviation (SD).

TABLE 10

Fluid affinity of hydrogel of invention and gel known from
WO 95/17166 against gelatine (Donation)

| Dressing | Concentration of gelatine (% w/w) | Absolute decrease in weight in gram | Percentage decrease in weight |
|---|---|---|---|
| Amorphous Hydrogel of invention | 35 | 1.07 | 10.68(0.20) |
| Gel known from WO 95/17166 | 35 | 1.12 | 11.18(0.22) |

Figures in parentheses designates standard deviation (SD).

EXAMPLE 10

In vivo comparison of a hydrogel according to the invention and IntraSite® Gel with respect to debriding effect, wear time and pain and ease of use.

32 patients having a leg ulcer were treated with a hydrogel according to the invention or IntraSite® Gel covered with a hydrocolloid dressing (COMFEEL+Dressing) or a film dressing (OpSite® Flexigrid) according to the evaluation by the physician.

Inclusion criteria were: patients with a clinically non-infected leg ulcer covered by necrosis and/or fibrin, patients more than 18 years of age.

Exclusion criteria: Erysipelas or other symptoms of clinical wound infections, active vasculitis, disease requiring systemic treatment with corticostreoids or other immunosuppressants, pregnancy and breast feeding.

The patients were randomised and treated for a period of 2–4 weeks and the wounds were evaluated weekly.

The weekly evaluation comprised:

Area covered by necrosis/fibrin, appearance of surrounding skin, dressing performance, pain experience during change of dressing, wear time, and photography.

Two patients treated with IntraSite® Gel dropped out due to an allergic reaction to the product.

There was a significant difference in the reduction of area covered with fibrin/necrosis. In the group treated with the hydrogel of the invention, the area was reduced during the first two weeks, whereas the area was almost constant during the first two weeks in the group treated with IntraSite® Gel whereafter a reduction of the area was seen.

No difference was detected between the groups with respect to appearance of surrounding skin.

With respect to ease of application, there was a significant difference in favour of the gel of the invention partly due to a high cohesion of the product and reduced tendency of flowing during application as compared to IntraSite® Gel.

The group treated with the hydrogel of the invention experienced a significantly lower pain during treatment than the group treated with Intrasite® Gel.

The median score of wear time was four days in the group treated with the hydrogel of the invention and three days in the group treated with IntraSite® Gel.

These results indicates a faster initiation of debridement when using the hydrogel of the invention and also a longer wear time.

What is claimed is:

1. A method for preparing a hydrocolloid gel formulation wherein a cross-linked water-swellable cellulose derivative powder is mixed dry with alginate powder and then water is admixed.

2. A method as claimed in claim 1 wherein the mixing is carried out using a dissolver.

3. Use of an amorphous hydrocolloid gel composition which comprises
    a. a water insoluble, water swellable cross-linked cellulose derivative
    b. an alginate; and
    c. distilled water in a sufficient amount to make up the difference between the amount of ingredients a.+b. and 100% and wherein the gel comprises from 0.05 to 5.00% by weight of alginate and from 2.00 to 8.00% by weight of cross-linked water swellable cellulose derivative for debridement of necrotic tissue in a wound and for speeding up the healing of the wound.

4. Use of an amorphous hydrocolloid gel composition which comprises
    a. a water insoluble, water swellable cross-linked cellulose derivative
    b. an alginate; and
    c. distilled water in a sufficient amount to make up the difference between the amount of ingredients a.+b. and 100% and wherein the gel comprises from 0.05 to 5.00% by weight of alginate and from 2.00 to 8.00% by weight of cross-linked water swellable cellulose derivative as vehicle for transplantation of cells to a wound.

5. A hydrocolloid gel composition which comprises
    a. a water insoluble, water swellable, cross-linked cellulose derivative;
    b. an alginate; and
    c. distilled water in a sufficient amount to make up the difference between the amount of ingredients a+b and 100% such that the gel includes from 0.05 to 5.00% by weight of the alginate and from 2.00 to 8.00% by weight of the water insoluble, water swellable cross-linked cellulose derivative.

6. A hydrocolloid gel composition as claimed in claim 5 which includes from 3 to 5% by weight of the water insoluble, water swellable, cross-linked cellulose derivative.

7. A hydrocolloid gel composition as claimed in claim 6 wherein the gel composition is a wound gel composition.

8. A hydrocolloid gel composition as claimed in claim 5 which includes from 0.5 to 1.00% by weight of the alginate.

9. A hydrocolloid gel composition as claimed in claim 8 wherein the gel composition is a wound gel composition.

10. A hydrocolloid gel composition as claimed in claim 5 which further includes an active ingredient.

11. A hydrocolloid gel composition as claimed in claim 10 wherein the gel composition is a wound gel composition.

12. A hydrocolloid gel composition as claimed in claim 5 wherein the gel composition is a wound gel composition.

* * * * *